United States Patent [19]

Suzuki

[11] 4,221,918

[45] Sep. 9, 1980

[54] PREPARATION OF DIESTERS

[75] Inventor: Shigeto Suzuki, San Francisco, Calif.

[73] Assignee: Chevron Research Company, San Francisco, Calif.

[21] Appl. No.: 956,018

[22] Filed: Oct. 30, 1978

[51] Int. Cl.$^2$ .................. C07C 67/00; C07C 69/16; C07C 69/28; C07C 69/74

[52] U.S. Cl. .................. 560/263; 260/345.8 R; 260/347.5; 260/410.6; 260/465 D; 260/465.4; 546/263; 560/1; 560/20; 560/21; 560/51; 560/55; 560/56; 560/64; 560/100; 560/104; 560/105; 560/106; 560/122; 560/126; 560/174; 560/187; 560/224; 549/59; 549/71

[58] Field of Search .................. 560/263, 1, 100, 105, 560/106, 122, 224; 260/410.6

[56] References Cited

U.S. PATENT DOCUMENTS 3,579,566  5/1971  Fenton .................. 560/263

FOREIGN PATENT DOCUMENTS 2016061  4/1970  Fed. Rep. of Germany .......... 560/263

*Primary Examiner*—Vivian Garner
*Attorney, Agent, or Firm*—D. A. Newell; John Stoner, Jr.

[57] ABSTRACT

Carboxylic acid anhydrides are contacted with hydrogen in the presence of an insoluble metal hydrogenation catalyst and strong protonic acid to produce 1,1-diesters.

7 Claims, No Drawings

PREPARATION OF DIESTERS

BACKGROUND OF THE INVENTION

1. Field of the Invention

The present invention relates to the preparation of diesters. More particularly, the invention relates to the preparation of 1,1-diesters by the direct hydrogenation of carboxylic acid anhydride in the presence of an insoluble metal hydrogenation catalyst and a strong protonic acid.

2. Description of the Prior Art 1,1-Diesters are useful intermediates and solvents. Ethylidene diacetate, for example, is a well-known compound classically prepared by the reaction of acetaldehyde and acetic anhydride. More recently, it has been prepared in homogeneous solution by the hydrogenation of acetic anhydride catalyzed by a soluble noble metal-biphyllic ligand complex (see U.S. Pat. No. 3,579,566). In this patented process, the noble metal catalyst is maintained in solution by a variety of biphyllic ligands, e.g., organic phosphines, arsines, or stilbenes, such as trimethyl phosphine, triphenyl phosphine, etc. Reaction conditions include temperatures of 50° C. to 250° C., pressures from 1 to 300 atmospheres, and from 0.002 to 2.0 weight percent noble metal catalyst. The examples show low conversions (66%) and yields (11%), even after reacting for 2 hours at 100° C. plus 2 hours at 200° C. under hydrogen pressures ranging from 800 to 1200 psi. The Rosenmund Reduction (reference: Organic Reactions, Vol. IV, J. Wiley and Sons, New York, 1948, p. 362) involves the hydrogenation of an acid chloride to an aldehyde over a suitable catalyst, usually palladium.

SUMMARY OF THE INVENTION

In accordance with the present invention, there is provided a heterogeneous process for preparing 1,1-diesters which comprises contacting a carboxylic acid anhydride with hydrogen in the presence of an insoluble metal hydrogenation catalyst and a strong protonic acid.

DETAILED DESCRIPTION OF THE INVENTION

The carboxylic acid anhydrides useful in this process include the usual anhydrides having the structure:

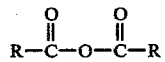

and ketene. In this formula, R is an alkyl group having from 1 to 20 carbon atoms, a cycloalkyl group having from 5 to 8 carbon atoms, an alkenyl or alkynyl group having from 2 to 20 carbon atoms, aryl or alkaryl groups having from 6 to 12 carbon atoms, aralkyl groups having from 7 to 12 carbon atoms, or a heterocyclic group of a 5- or 6-membered ring.

The aryl groups in the above definition of R are optionally substituted with halogens such as chlorine, a nitro group, an alkoxy group of 1 to 4 carbon atoms, a nitrile group, or an acyl group. The aliphatic groups are optionally substituted with an alkoxy group of 1 to 4 carbon atoms, a nitrile group, or a ketone carbonyl group.

Typical alkyl groups are methyl, ethyl, propyl, hexadecyl, dodecyl and eicosyl; typical cycloalkyl groups are cyclopentyl, cyclohexyl and cyclooctyl; typical alkenyl groups are vinyl, allyl, crotyl, linolenyl, delta$^{9,10}$-decylenyl and oleyl; typical alkynyl groups are propargyl and delta$^{9,10}$-decylnyl; typical aryl and alkaryl groups are phenyl, tolyl, p-ethylphenyl, p-chlorophenyl, xylyl, naphthyl and 3-dodecylphenyl; typical aralkyl groups are 2-phenylethyl, 12-tolyldodecyl, 2-(2'-naphthyl)propyl, phenylmethyl and 4-chlorophenylmethyl; and typical heterocyclic groups include furyl, thienyl and pyranyl.

Acid anhydrides useful as feedstocks to the present process include: acetic anhydride, propionic anhydride, stearic anhydride, arachidic anhydride, acrylic anhydride, oleic anhydride, linoleic anhydride, tariric anhydride, benzoic anhydride, toluic anhydride, naphthoic anhydride, phenylacetic anhydride, cinnamic anhydride, furoic anhydride, nicotinic acid anhydride, and the like.

Ketene is a dehydrated form of acetic acid and is a satisfactory feed supplement for the present process. As such it is used with at least an equimolar amount of acetic anhydride.

The preferred anhydrides are the fatty acid anhydrides, in particular acetic anhydride.

The insoluble hydrogenation metal catalysts include the metals of Group VIII such as palladium, platinum, osmium, ruthenium, nickel, cobalt, etc.; and the transition metals such as chromium, copper, etc. The metal catalysts are used as fine powders or, preferably, they are in the form of a metallic layer on a support. Suitable supports include carbon, alumina, silica, kieselguhr, barium sulfate, and the like. The preferred catalyst is palladium on charcoal. These catalysts are insoluble in the reaction medium and, hence, the reaction is heterogeneous.

The strong protonic acids useful in this process are those having a pKa less than 6, preferably less than 4. The inorganic protonic acids include the hydrogen halide acids, i.e., hydrogen fluoride, hydrogen chloride, hydrogen bromide and hydrogen iodide; also included are sulfuric acid, phosphoric acid and chlorosulfonic acid. The strong organic protonic acids include methanesulfonic acid, trifluoromethanesulfonic acid, p-toluene sulfonic acid, trifluoroacetic acid and trichloroacetic acid. The preferred protonic acids are hydrogen chloride, methanesulfonic acid and hydrogen fluoride.

The strong protonic acids are preferably added to the reaction system as such, but they may also be formed in situ. For example, aluminum chloride in the presence of hydrogen will liberate sufficient hydrogen chloride to catalyze the reaction. In general, Lewis acids are useful additives to the reaction system to increase the rates. Lewis acids that liberate a strong protonic acid upon reaction with hydrogen may be used alone; other Lewis acids must be used with protonic acids.

Similarly, organic compounds that give a strong protonic acid upon reaction with hydrogen may be used as an in-situ source of acid. For example, acetyl chloride may be added to the reaction system to furnish hydrogen chloride.

The amount of strong protonic acid to be used in this reaction is based on the quantity of carboxylic acid anhydride and ranges from 0.0001 to 0.5, preferably 0.001 to 0.3, mol per mol of anhydride.

Reaction temperatures range from 20° C. to 200° C., preferably from 50° C. to 150° C. Low temperatures require fairly long reaction times in the order of 12 to 24 hours, whereas the higher temperatures of 50° C. or more require reaction times of less than 10 hours, usually from 1 to 5 hours.

The reaction takes place readily at atmospheric pressure with gaseous hydrogen bubbling through the liquid reaction system. However, superatmospheric pressure may be used to improve the efficiency of hydrogen utilization and to improve the rate of reaction. Pressures up to 2000 psig are satisfactory. Higher pressures may give some hydrogenation of the organic products. Therefore, it is preferred to carry out the reaction at pressures in the range of 0 to 1000 psig.

The hydrogen used in this process is preferably pure hydrogen, but it may contain up to 50 volume percent of inert additives. In particular, it may be a synthesis gas containing from 10 to 50% carbon monoxide.

The reaction may be carried out in either batch or continuous processes. In the batch system, the anhydride, the metal catalyst and the protonic acid are all charged to a reaction vessel. The hydrogen may be passed through the reactor contents at atmospheric pressure and at the desired temperature or, preferably, the reactor may be closed and the hydrogen added to maintain a desired pressure. Alternatively, the protonic acid in the vapor form may be added with the hydrogen. On the other hand, a continuous process is contemplated wherein hydrogen gas is passed through a supported metal catalyst-packed reactor cocurrently or countercurrently to the flow of the anhydride. The protonic acid may be dissolved in the anhydride or, if the acid is gaseous, in the hydrogen.

In either process, the product is used as is or, if necessary, is separated from the crude reaction mixture and recovered by distillation. The catalyst is removed by filtration or centrifugation. Preferably the protonic acid is removed by low-temperature stripping or neutralization before distillation is started. Any unreacted anhydride is also recoverable and available for recycle.

While it is preferred to carry out this process neat, a solvent may be employed. A wide range of non-reactive, inert organic liquids are satisfactory solvents. Included among the useful solvents are the aromatic and aliphatic hydrocarbons such as toluene, xylene, octane, etc.; esters such as ethyl acetate, cyclohexyl acetate, methyl benzoate, methyl succinate, etc.; ketones such as acetophenone, acetone, cyclohexanone, etc.; ethers such as diethyl ether, tetrahydrofuran, anisole, etc.; carboxylic acids, such as acetic acid, propionic acid, etc.; and nitriles such as acetonitrile, benzonitrile, etc. Preferably, when a carboxylic acid is used as a solvent, it is of the same acid as is in the anhydride feed. The solvents are chosen to have a boiling point different from that of the product, and preferably a higher boiling point. Thus, the product can be recovered by distillation, leaving the solvent bottoms available for recycle.

EXAMPLES

The process of the present invention is illustrated by the following examples. Unless otherwise specified, the proportions in the examples are on a weight basis.

EXAMPLE 1

A 300-ml round-bottom flask equipped with a thermometer, stirrer, gas inlet tube, and condenser was charged with 76.5 g (0.75 mol) of acetic anhydride and 0.3 g of a 5% palladium-on-carbon catalyst. The contents were heated to 70° C. and hydrogen, containing 10% (volume) of hydrogen chloride, was added through the gas inlet tube at 110 ml per minute. After 2 hours, a gas-chromatographic analysis of an aliquot of the total reaction mixture showed 23% conversion of anhydride. The anhydride-free product contained 17% ethylidene diacetate, 74% acetic acid and 9% ethylidene chloride acetate (1-chloromethyl acetate) (measured as area percent).

The reaction was then continued for an additional 7 hours at 90° C. Analysis of the final mixture showed 100% conversion of anhydride. The product contained about 45% each of ethylidene diacetate and acetic acid, and the remainder ethylidene chloride acetate.

The crude reaction mixture was then filtered to remove the insoluble catalyst. The filtrate was stripped of hydrogen chloride by passing nitrogen through the mixture at room temperature. The stripped mixture was distilled to give 35 g (64 mol percent stoichiometric yield) of ethylidene diacetate, having a boiling point of 56° C. at 10 mm pressure. There was no high-boiling by-product.

In the following experiments, analysis is by gas chromatography, and the results are reported as area percent of the chromatograph trace.

EXAMPLE 2

A 300-ml Fisher-Porter bottle was charged with 61.2 g (0.60 mol) of acetic anhydride, 0.3 g of a 5% palladium-on-carbon catalyst, and 0.8 g of acetyl chloride. The bottle was pressurized to 80–95 psig with hydrogen. After 4 hours at 90° C., a gas chromatographic analysis showed 18% conversion, with about equal amounts of ethylidene diacetate and acetic acid formed.

EXAMPLE 3

This example was carried out essentially the same as Example 1, except that no hydrogen chloride was added. After 6 hours at 90° C., there was no evidence of reaction.

EXAMPLE 4

This example was carried out essentially the same as Example 2, except that 7.9 g of acetyl chloride was used. Aliquots were analyzed periodically to give the results shown in Table I.

TABLE I

|  | Sample 1 | Sample 2 | Sample 3 |
|---|---|---|---|
| Reaction Time (Hours) | 4 | 8 | 13 |
| Reaction Mixture Composition (area percent) |  |  |  |
| Acetic Anhydride | 42 | 13 | 3 |
| Ethylidene Diacetate | 31 | 49 | 52 |
| Acetic Acid | 19 | 28 | 31 |
| Ethylidene Chloride Acetate | 7 | 8 | 11 |

EXAMPLE 5

This example was carried out essentially the same as Example 1, except that the hydrogen chloride was replaced by an equal volume of hydrogen bromide and the temperature was 90° C. throughout the reaction. The results are given in Table II.

TABLE II

|  | Sample 1 | Sample 2 | Sample 3 |
|---|---|---|---|
| Reaction Time (Hours) | 3 | 7 | 11 |
| Reaction Mixture Composition (area percent) |  |  |  |

TABLE II-continued

|  | Sample 1 | Sample 2 | Sample 3 |
|---|---|---|---|
| Acetic Adhydride | 66 | 38 | 26 |
| Ethylidene Diacetate | 19 | 28 | 32 |
| Acetic Acid | 15 | 33 | 39 |

EXAMPLE 6

This example was essentially the same as Example 5, except that the hydrogen bromide was replaced by an equal amount of hydrogen iodide. After 3 hours, the reaction mixture contained 89% acetic anhydride, 3% ethylidene diacetate and 7% acetic acid.

EXAMPLE 7

This example was essentially the same as Example 1, except that 3.0 g of a 5% palladium-on-carbon catalyst was used, the temperature was 90° C. throughout and the exit gas stream was passed through $CO_2$-cooled traps. The results are given in Table III.

TABLE III

|  | Sample 1 | Sample 2 | Sample 3 |
|---|---|---|---|
| Reaction Time (Hours) | 4 | 8 | 11 |
| Reaction Mixture Composition (area percent) |  |  |  |
| Acetic Anhydride | 40 | 22 | 7 |
| Ethylidene Diacetate | 21 | 27 | 33 |
| Acetic Acid | 33 | 47 | 57 |
| Ethylidene Chloride Acetate | 5 | 4 | 0.7 |

In addition, there were 12 grams of acetyl chloride in the traps.

EXAMPLE 8

This example was carried out as in Example 2, except that 2.5 g of 5% palladium-on-carbon catalyst were used and 2.9 g of methanesulfonic acid were charged to the reactor. After 7 hours at 90° C., the reaction mixture contained 7.6% acetic anhydride, 62.8% ethylidene diacetate, and 27% acetic acid.

EXAMPLE 9

This example was carried out essentially the same as Example 8, except that only 1.5 g of 5% palladium-on-carbon catalyst was employed and the methanesulfonic acid was replaced by 4.1 g of hydrogen chloride. The results are given in Table IV.

TABLE IV

|  | Sample 1 | Sample 2 | Sample 3 |
|---|---|---|---|
| Reaction Time (Hours) | 3 | 7 | 12 |
| Reaction Mixture Composition (area percent) |  |  |  |
| Acetic Anhydride | 53 | 38 | 29 |
| Ethylidene Diacetate | 16 | 24 | 29 |
| Acetic Acid | 25 | 30 | 33 |
| Acetyl Chloride | 1 | 3 | 2 |
| Ethylidene Chloride Acetate | 3 | 4 | 5 |

EXAMPLE 10

This example was carried out as in Example 8 except that the methanesulfonic acid was replaced by 2.9 g of 98% sulfuric acid. After 11 hours at 90° C., the reaction mixture contained 9.9% acetic anhydride, 35.2% ethylidene diacetate, and 42.6% acetic acid.

EXAMPLE 11

A 300-ml Hastelloy autoclave with a magnetic stirrer was charged with 61.2 g (0.60 mol) of acetic anhydride, 1.5 g of a 5% palladium-on-carbon catalyst, and 4.0 g (0.11 mol) HCl. The autoclave was pressurized to 80–95 psig with hydrogen. After 6 hours at 90° C., a gas chromatographic analysis of the product with para-dioxane as an internal standard showed 93.4% acetic anhydride conversion, 75.4 mol percent selectivity to ethylidene diacetate and 19.5 mol percent selectivity to ethylidene chloride acetate.

EXAMPLE 12

This experiment was carried out essentially the same as Example 11, except that the hydrogen chloride was replaced by 6.0 g (0.06 mol) methanesulfonic acid. After 3 hours, a gas chromatographic analysis of the reaction product (after a sodium acetate treatment to neutralize methanesulfonic acid catalyst) with added para-dioxane as an internal standard showed 96.5 mol percent acetic anhydride conversion and 98.2 mol percent selectivity to ethylidene diacetate.

EXAMPLE 13

This experiment was carried out essentially the same as Example 11, except that the hydrogen chloride was replaced by 7.6 g (0.12 mol) acetyl fluoride as a hydrogen fluoride source, and higher hydrogen pressure and temperature were used. At 90° C. and 160 psig hydrogen pressure, hardly any hydrogen uptake was observed after 1.5 hours. Then the pressure was raised to 1000 psig at 90° C., and again hardly any hydrogen uptake was observed in 1 hour. When the temperature was raised to 130° C. at 1000 psig hydrogen pressure, a calculated amount of hydrogen was taken up in 2 hours. A gas chromatographic analysis of the product with a para-dioxane internal standard showed >99% acetic anhydride conversion, 95.1 mol percent selectivity to ethylidene diacetate, and 2% selectivity to ethyl acetate.

EXAMPLE 14

This experiment was essentially the same as Example 11, except that the 5% palladium-on-carbon catalyst was replaced by 3.0 g Raney nickel (prewashed with acetic anhydride), and higher hydrogen pressure and temperature were used. At 30° C. and 130 psig hydrogen pressure for 0.5 hour and further at 60° C. and 1000 psig hydrogen pressure for 0.6 hour, hardly any hydrogen uptake was observed. At 90° C. and 1000 psig hydrogen pressure, about 20% hydrogen uptake was observed in 2.5 hours, and further at 120° C. and 1000 psig hydrogen pressure about 15% more hydrogen uptake was observed in 0.6 hour. A gas chromatographic analysis of this product as before showed 33% acetic anhydride conversion, 76 mol percent selectivity to ethylidene diacetate, 3.6% selectivity to ethylidene chloride acetate, and 1.5% selectivity to acetyl chloride.

EXAMPLE 15

A 300-ml Hastelloy stirred autoclave was charged with 78.0 g (0.60 mol) propionic anhydride, 5% palladium on carbon and 6.0 g (0.06 mol) methanesulfonic acid. The mixture was stirred at 90° C. under an 80–130 psig hydrogen pressure for 5 hours, and during the period approximately 90% of the calculated amount of the hydrogen was taken up. A gas chromatographic analysis of the product mixture using a dioxane internal standard showed 84 mol percent propionic anhydride conversion with 58 mol percent selectivity to propylidene dipropionate.

The above experiments illustrate many of the ways in which this inventive process can be carried out in order to produce ethylidene diacetate, and other 1,1-diesters.

While the character of this invention has been described in detail with illustrative examples, this has been done by way of illustration only and without limitation of the invention. It will be apparent to those skilled in the art that modifications and variations of the illustrative examples may be made in the practice of the invention within the scope of the following claims.

What is claimed is:

1. A heterogeneous process for preparing 1,1-diesters which comprises contacting a carboxylic acid anhydride with hydrogen in the presence of an insoluble metal hydrogenation catalyst and a strong protonic acid having a pKa of less than 4, said carboxylic acid anhydride being selected from the group consisting of anhydrides having the structure

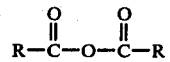

wherein R is an alkyl group having from 1 to 20 carbon atoms, a cycloalkyl group having from 5 to 8 carbon atoms, an alkenyl or alkynyl group having from 2 to 20 carbon atoms, aryl or alkaryl groups having from 6 to 12 carbon atoms, or aralkyl groups having from 7 to 12 carbon atoms.

2. A process according to claim 1 wherein the carboxylic acid anhydride is a fatty acid anhydride.

3. A process to claim 2 wherein the carboxylic acid anhydride is acetic anhydride.

4. A process according to claim 3 wherein the insoluble metal hydrogenation catalyst is palladium on charcoal.

5. A process according to claim 4 wherein the strong protonic acid is hydrogen chloride.

6. A process according to claim 4 wherein the strong protonic acid is methanesulfonic acid.

7. A process according to claim 4 wherein the strong protonic acid is hydrogen fluoride.

* * * * *

UNITED STATES PATENT AND TRADEMARK OFFICE
CERTIFICATE OF CORRECTION

PATENT NO. : 4,221,918
DATED : September 9, 1980
INVENTOR(S) : Shigeto Suzuki

It is certified that error appears in the above-identified patent and that said Letters Patent are hereby corrected as shown below:

Col. 3, line 20, "The" should read --Then--.

Col. 8, line 13, "to" should read --according to--.

Signed and Sealed this

Third Day of February 1981

[SEAL]

Attest:

RENE D. TEGTMEYER

Attesting Officer       Acting Commissioner of Patents and Trademarks